(12) United States Patent
Stroebech et al.

(10) Patent No.: US 11,109,996 B2
(45) Date of Patent: Sep. 7, 2021

(54) OSTOMY APPLIANCE WITH A RELEASE LINER WITH AN ENCLOSURE

(71) Applicant: Coloplast A/S, Humlebaek (DK)

(72) Inventors: Esben Stroebech, Hoersholm (DK);
Michael Hansen, Gilleleje (DK);
Birthe Vestbo Andersen, Espergaerde (DK); Peter Kwok Hing Lam, Frederiksberg C (DK); Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 740 days.

(21) Appl. No.: 15/761,812

(22) PCT Filed: Sep. 23, 2016

(86) PCT No.: PCT/DK2016/050306
§ 371 (c)(1),
(2) Date: Mar. 21, 2018

(87) PCT Pub. No.: WO2017/050340
PCT Pub. Date: Mar. 30, 2017

(65) Prior Publication Data
US 2018/0263804 A1 Sep. 20, 2018

(30) Foreign Application Priority Data

Sep. 24, 2015 (DK) .......................... PA 2015 70609
Oct. 8, 2015 (DK) .......................... PA 2015 70 637
Nov. 10, 2015 (DK) .......................... PA 2015 70725

(51) Int. Cl.
*A61F 5/443* (2006.01)
*A61F 5/445* (2006.01)
*A61F 5/44* (2006.01)

(52) U.S. Cl.
CPC ............ *A61F 5/443* (2013.01); *A61F 5/4404* (2013.01); *A61F 5/445* (2013.01)

(58) Field of Classification Search
CPC combination set(s) only.
See application file for complete search history.

(56) References Cited

U.S. PATENT DOCUMENTS 5,175,246 A * 12/1992 Smith .................. A61K 9/7061
523/111
5,678,564 A * 10/1997 Lawrence ............... A61F 5/455
600/574

(Continued)

FOREIGN PATENT DOCUMENTS

CN        1233945 A     11/1999
CN        1338916 A      3/2002

(Continued)

*Primary Examiner* — Guy K Townsend
(74) *Attorney, Agent, or Firm* — Coloplast Corp., Coloplast A/S; Nick Baumann

(57) ABSTRACT

An ostomy appliance comprising an adhesive wafer (2) for attachment to a skin surface of a user. The adhesive wafer includes a backing layer (13), an adhesive layer (12), and at least one release liner (17). The release liner comprises an enclosure (9) capable of containing a liquid or a wipe (14). The enclosure (9) can be filled with liquid before removal from the wafer, thereby providing a temperature impact on the adhesive. The wipe (14) can be impregnated with an activating agent for providing an activation of the adhesive prior to use.

12 Claims, 8 Drawing Sheets

(56) References Cited

U.S. PATENT DOCUMENTS

| | | | |
|---|---|---|---|
| 6,332,879 B1* | 12/2001 | Nielsen | A61F 5/448 604/344 |
| 6,336,920 B1* | 1/2002 | Temple | A61F 5/44 604/339 |
| 10,294,333 B2* | 5/2019 | Liu | C09J 183/10 |
| 2002/0013568 A1* | 1/2002 | Cinelli | A61L 15/58 604/387 |
| 2002/0037977 A1* | 3/2002 | Feldstein | A61L 15/58 526/60 |
| 2007/0117880 A1* | 5/2007 | Elson | A61F 5/453 523/118 |
| 2007/0202245 A1* | 8/2007 | Gantner | A61L 15/58 427/2.1 |
| 2007/0231571 A1* | 10/2007 | Lane | C09J 7/38 428/354 |
| 2009/0240219 A1* | 9/2009 | Barcroft | A61F 5/4404 604/332 |
| 2014/0114265 A1* | 4/2014 | Israelson | A61F 5/443 604/342 |
| 2015/0141944 A1* | 5/2015 | Hanuka | B31B 50/26 604/337 |
| 2015/0376345 A1* | 12/2015 | Liu | C08L 83/00 428/345 |

FOREIGN PATENT DOCUMENTS

| | | | | |
|---|---|---|---|---|
| CN | 201320237 Y | 10/2009 | | |
| CN | 101765417 A | 6/2010 | | |
| CN | 203598093 U | 5/2014 | | |
| EP | 2726030 B1 | 8/2015 | | |
| FR | 2533821 A3 * | 4/1984 | | A61F 5/445 |
| FR | 2533821 A3 | 4/1984 | | |
| GB | 2458477 * | 9/2009 | | A61F 5/445 |
| GB | 2458477 A1 | 9/2009 | | |
| JP | 10323370 A2 | 12/1998 | | |
| RU | 2220685 C1 | 1/2004 | | |
| WO | 9511644 A1 | 5/1995 | | |
| WO | WO199511644 A2 * | 5/1995 | | A61F 5/4404 |

* cited by examiner

OSTOMY APPLIANCE WITH A RELEASE LINER WITH AN ENCLOSURE

SUMMARY OF THE INVENTION

Disclosed is an ostomy appliance comprising an adhesive wafer for attachment to a skin surface of a user. The adhesive wafer includes a backing layer, an adhesive layer, and at least one release liner. The release liner comprises an enclosure.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

DETAILED DESCRIPTION OF THE INVENTION

Figure 1:
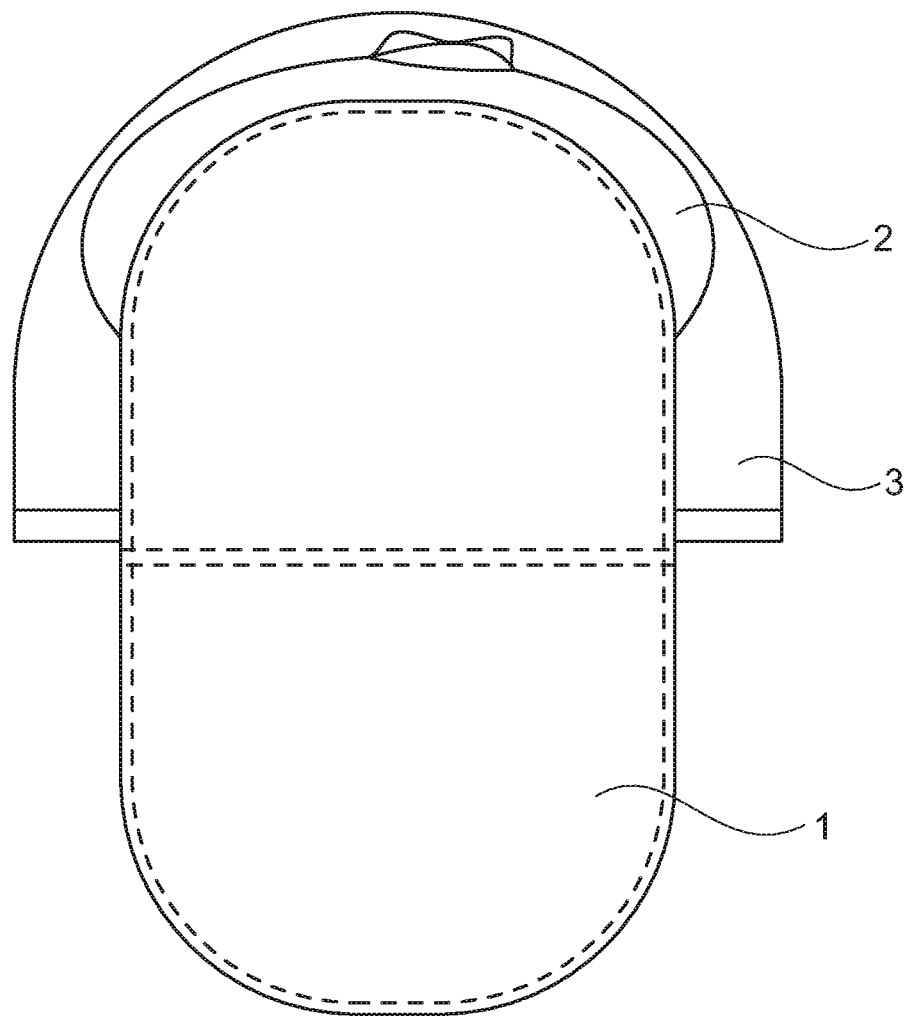
In FIG. 1 is shown an ostomy appliance with a release liner comprising an enclosure, seen from the distal side, In FIG. 2 is shown an exploded view of a release liner.

Embodiments provide an ostomy appliance comprising an adhesive wafer for securing the appliance to the skin, the wafer comprising an adhesive layer, a backing layer covering the distal surface of the adhesive layer; a release liner is covering the proximal surface of the adhesive layer before use, wherein said release liner comprises an enclosure.

When referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

"Release liner" is intended to define a liner covering the proximal (skin contacting) side of the adhesive wafer that ensures at least that the properties of the adhesive are preserved and that the adhesive surface is not laid open until just before the use.

In embodiments, the release liner comprises an enclosure capable of containing a liquid or a wipe.

In embodiments, the release liner comprises an enclosure made from a liquid impermeable material, such as a film or foil of plastic or metal or a laminate thereof. As used herein, liquid impermeable means that liquid, such as water, is rejected from penetrating the material by simple flow.

In embodiments, the release liner comprises of one or more layers of polymer film sealed together to form an enclosure. The sealing may be any suitable sealing such as an adhesive sealing or a welding. When the enclosure is empty, the release liner may be substantially two-dimensional, thereby taking up less space during storage.

In embodiments, the enclosure provided in the release liner of the ostomy appliance makes it possible to bring a substance, such as a liquid, into close proximity with the adhesive surface that is to be attached to the skin. This means that a substance in the enclosure can affect the adhesive, for instance by heating it. As an example, a warm substance, such as warm water, provided in the enclosure can heat the adhesive in order to affect the properties of the adhesive. For instance, such heating can lead to increased tack or decreased viscosity of the adhesive, potentially making the adhesive easier to attach to the skin.

The enclosure may be provided with an inlet for entering liquid into the enclosure. The inlet facilitates pouring liquid into the enclosure. In embodiments, the inlet may comprise sealing means providing a sealing of the enclosure. The sealing means may be a one-way valve or a non-return valve, such as a foil valve. The sealing may be fluid-tight or it may be substantially fluid-tight in the sense that it keeps a majority of the liquid from escaping from the enclosure.

In embodiments, the enclosure is sealed along the entire edge to provide a fluid-tight enclosure. This enables the enclosure to be delivered containing a substance or a wipe. The sealing of the enclosure may be fully or partly peelable in order to be able to retrieve the enclosed wipe or substance.

In embodiments, the sealing means is a zip lock. Such lock may enable having abroad inlet yet being easy to close fluid-tight. A broad opening facilitates easy filling with liquid as well as the enclosure after use may be used for other purposes such as for disposals.

In embodiments, the inlet comprises a funnel. The funnel enables easy filling of the enclosure and may provide space for sealing means.

In embodiments, the inlet can be enlarged by peeling a sealing around the inlet. The sealing at the portion of the enclosure surrounding the inlet may be made as a peelable sealing, thereby enabling enlarging the inlet to be broader. The inlet may be enlarged after removal of the release liner from the adhesive surface to provide a bag for containing waste articles such as a used ostomy bag, thereby providing a hygienic disposal of such articles.

In embodiments, the enclosure has a size (surface area) corresponding to at least the adhesive surface of the wafer. This ensures that the entire adhesive surface is exposed to an impact of the liquid when the enclosure is filled.

In embodiments, the enclosure has a size (surface area) being smaller than the adhesive surface of the wafer. This enables that only a part of the adhesive surface is exposed to an impact from the contents of the enclosure.

In embodiments, the adhesive surface of the wafer comprises two or more release liners. In embodiments, a first release liner covers the central portion of the wafer and a second release liner covers the peripheral portion of the wafer.

In embodiments, the release liner has a size (surface area) extending further than the adhesive surface of the wafer. The enclosure may have the same size as the release liner, thus the entire release liner is an enclosure or the release liner may be larger than the enclosure. The release liner may extend further than the enclosure in one or more directions. The extended portions of the release liner may provide easy detachment of the release liner.

In embodiments, the enclosure is capable of self-standing when filled with liquid. By self-standing is meant that when the wafer, with a fluid filled enclosure, is placed in vertical position on a surface, for example a table, the wafer including the release liner is able to maintain stable in its vertical position without further support. The wafer being self-standing ensures that any air in the bag gathers at the top.

By vertical is herein meant a substantially upright position whereas by horizontal is herein meant the wafer is in a lying position.

In embodiments, the enclosure is extending further in one direction, such as upwards, than the adhesive surface in order to provide room for any trapped air. In embodiments, the release liner comprises an air compartment in fluid connection with the enclosure such that any air in the enclosure may gather in the air compartment instead of in the enclosure. In embodiments, an air compartment may gather any trapped air in the enclosure when the wafer with release liner is placed in horizontal position.

In embodiments, the enclosure may comprise anti-ballooning means. By anti-ballooning means is meant means ensuring that the enclosure remains in a substantially flat condition when filled with liquid instead of turning into a round structure (balloon). Such means may be in the form of a wall, layer, or other structure dividing the enclosure into two or more compartments. Anti-ballooning means may also take the form of internal welding dot and/or lines connecting the film layers of the enclosure inside the enclosure.

In embodiments, the adhesive is sensitive to temperature changes. Some adhesives are sensitive to temperature changes; they may for example become softer or more liquid at higher temperatures. To provide good adhesion to the skin around a stoma, the adhesive may be heated by entering warm or hot liquid into the enclosure of the release liner, letting the warm liquid heat the adhesive for a predetermined temperature, and then remove the release liner and apply the wafer to the skin. In embodiments, the appliance may be provided with an indicator showing when a predetermined temperature of the wafer is reached.

In embodiments, the adhesive is a heat switchable adhesive for example as the adhesives disclosed in U.S. Pat. No. 5,387,450.

In embodiments, the adhesive may be sensitive to contact with an activating agent. Such agent may for example be brought into contact with the adhesive by use of a wipe being impregnated with the agent.

In embodiments, the release liner may be provided with a release surface enabling the adhesive to be detached easily from the release liner. The release surface may be in the form of a coating or the release liner may comprise a material with release properties or it may be a separate release sheet attached to the release liner. The release sheet may have a size corresponding essentially to the adhesive surface of the wafer or it may be larger.

Embodiments provide a method of applying an ostomy appliance comprising the steps of:
a. providing an ostomy wafer comprising an adhesive layer, the distal surface of the adhesive layer is covered by a backing layer,
b. covering the proximal adhesive surface of the adhesive wafer with a release liner, said release liner comprises an enclosure capable of containing a liquid,
c. filling liquid into the enclosure of the release liner,
d. placing the adhesive wafer in such a way that the liquid in the enclosure covers the entire adhesive surface of the wafer,
e. removing the release liner and
f. applying the wafer to the skin.

In embodiments, the wafer is vertically positioned in step d. The enclosure may be self-standing.

Embodiments provide a method of applying an ostomy appliance comprising the steps of:
a. providing an ostomy appliance as disclosed herein,
b. filling liquid into the enclosure of the release liner, thereby bringing the liquid into proximity with the proximal surface of the adhesive layer,
c. removing the release liner, and
d. applying the adhesive wafer to the skin.

In embodiments, the enclosure is closed fluid tight before step c., facilitating possible placing of the appliance in horizontal position in step d without spilling liquid.

In embodiments, the enclosure is emptied after removal from the wafer and the inlet is enlarged by peeling. The enclosure may then be used for disposed articles such as a used ostomy bag.

In embodiments, the liquid is water. In embodiments, the liquid is hot or warm, such as hot water, for example hot tap water. In embodiments, the temperature of the liquid is different from the ambient temperature.

In embodiments, the enclosure contains a first composition capable of producing a temperature change when brought into contact with a second composition. In embodiments, the first composition is calcium chloride and the second composition is water. The calcium chloride may be present in the enclosure as a powder, whereas the water may be present in a closed sachet that can be ruptured from outside the enclosure, e.g. by pressing the sachet until it burst and the water flows out. When the calcium chloride is wetted by the water it develops heat, resulting in a hot liquid in the enclosure. The enclose may remain sealed during the process, thus the contents of the enclosure do not escape.

In embodiments, the enclosure contains an iron compound such as iron oxide. Iron powder which reacts with the oxygen in the air to yield iron oxide and heat, can be kept in a microporous pouch which are stored in a sealed compartment prior use.

In embodiments, the enclosure comprises an electric heating system that is capable of producing heat when activated. In embodiments, it is in the form of a battery pack in which its terminals are connected via a resistance to generate heat. In embodiments, the enclosure contains a composition capable of producing a temperature change when brought into contact with a second composition. In embodiments, before use, a liquid—being the second composition—is poured into the enclosure and heat is developed.

In embodiments, the enclosure comprises a wipe. By wipe is herein meant a sheet of absorbing material such as a Kleenex, gauze, foam, fabric, non-woven or other suitable materials. The wipe may be impregnated with an activating agent. By activating agent is herein meant a substance being capable of providing a change in the properties of an adhesive, for example change the adhesive tack or viscosity of the adhesive. Before use, the release liner comprising the enclosure may be removed from the adhesive surface, the enclosure may be peeled open, the wipe taken out and brought into contact with the thus exposed adhesive surface. The activating agent activated the adhesive by contact and the wafer can subsequently be applied to the skin.

In embodiments, the release liner comprising the enclosure may be smaller than the adhesive surface of the wafer, thereby only covering a part of the adhesive surface. The remaining adhesive surface may be covered with one or more other release liners.

Embodiments provide an ostomy kit comprising an ostomy wafer comprising an adhesive layer, the adhesive layer being covered on the distal surface by a backing layer, and a release liner, provided with a surface with release properties and said release liner being in the form of an enclosure capable of containing a liquid.

Embodiments provide a method of applying an ostomy appliance comprising the steps of:
a. providing an ostomy wafer comprising an adhesive layer, the distal surface of the adhesive layer is covered by a backing layer,
b. covering the proximal adhesive surface of the adhesive wafer with a release liner, said release liner comprises an enclosure capable of containing a wipe,
c. placing part of the release liner in such a way that the wipe is brought into contact with the entire adhesive surface of the wafer,
d. removing the release liner and
e. applying the wafer to the skin.

In embodiments, step c further comprises the step of removing part of the release liner prior to bringing another part of the release liner including the enclosure with the wipe into contact with the adhesive surface of the wafer.

DETAILED DESCRIPTION OF THE DRAWING

Embodiments, and features of the various exemplary embodiments described in this application, may be combined with each other ("mixed and matched"), unless specifically noted otherwise.

In FIG. 1 is shown an ostomy appliance seen from a distal side comprising a collection bag 1, and adhesive wafer 2 and a release liner 3.

Figure 2:
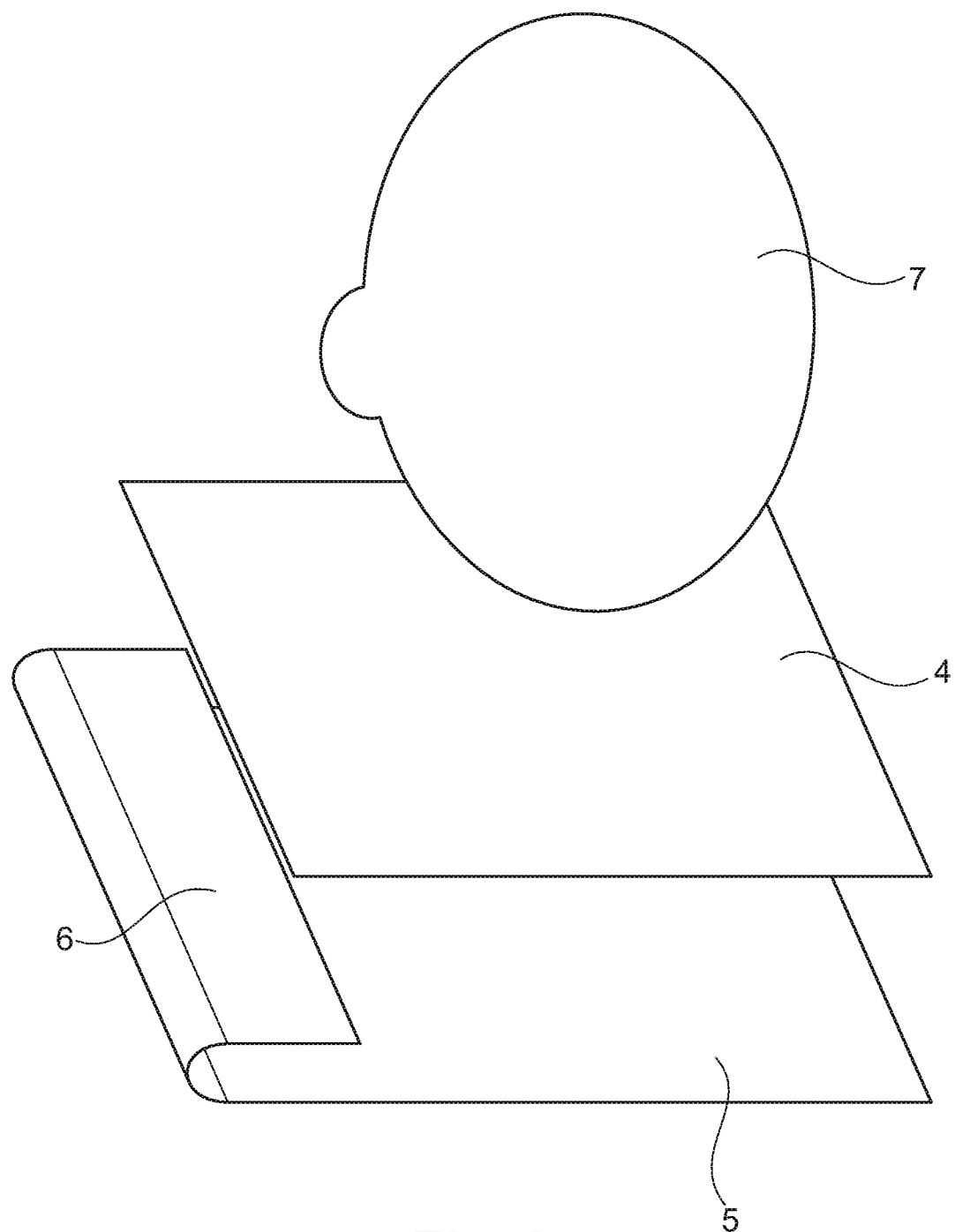
Figure 3:
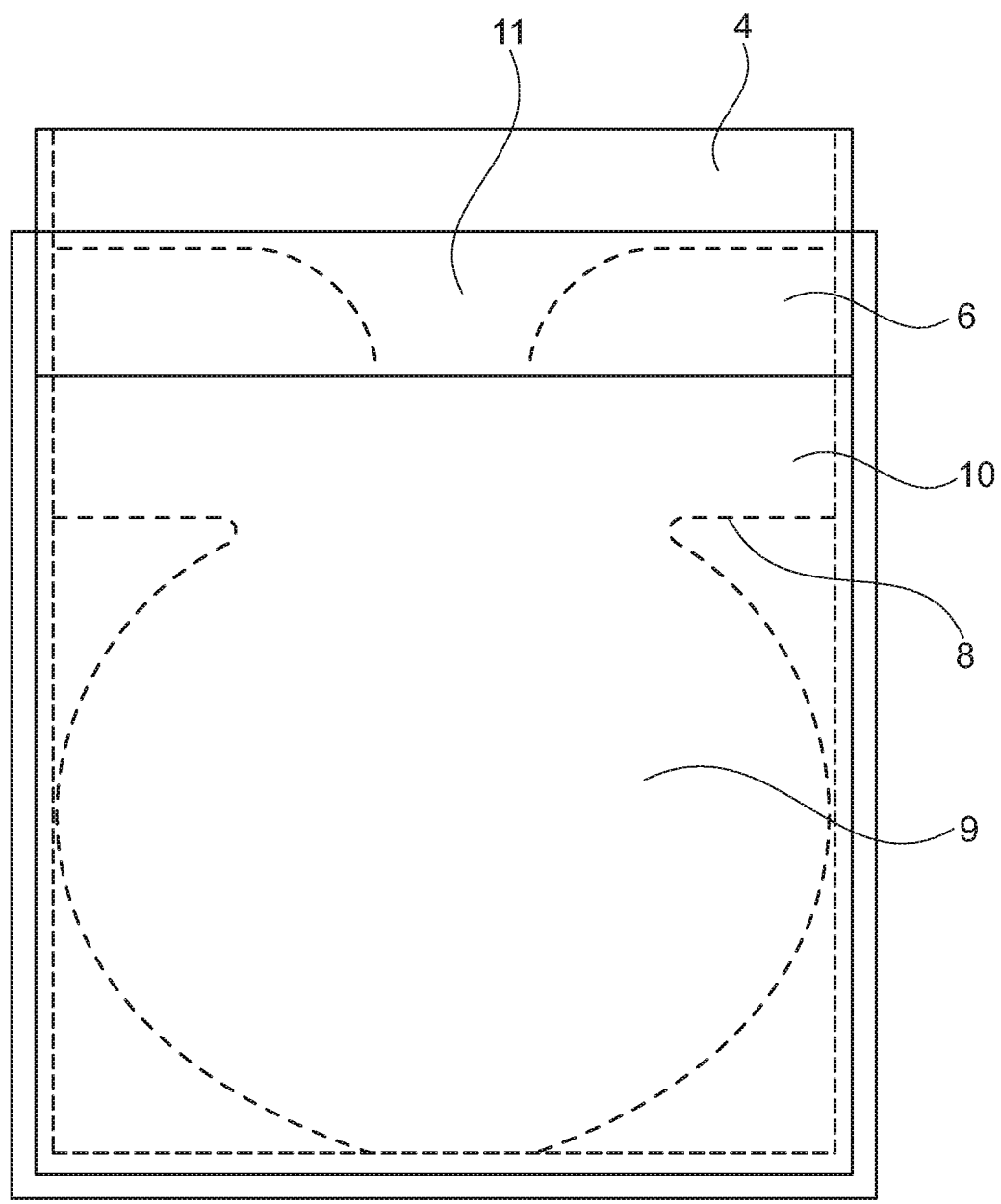
In FIG. 3 is shown a release liner seen from the front.

In FIG. 2 is shown an exploded view of a release liner 3. The release liner comprises a first wall 4 and a second wall 5 and a release sheet 7. The second wall is folded at the top 6 to provide a non-return valve. The release sheet 7 is attached to the first wall 4 by adhesive or welding or it may be in the form of a coating directly on the first wall 4. The first and the second walls are welded together as shown in FIG. 3, where the dotted lines indicate welding lines. The welding lines define an enclosure 9 substantially of the size and shape of the adhesive surface, and is fluidly connected to an air compartment 10. At the top of air compartment 10 is welded lines in funnel shape to provide an inlet 11. The inwards welding line shown as 8 separates the enclosure 9 for the air compartment 10.

Figure 4:
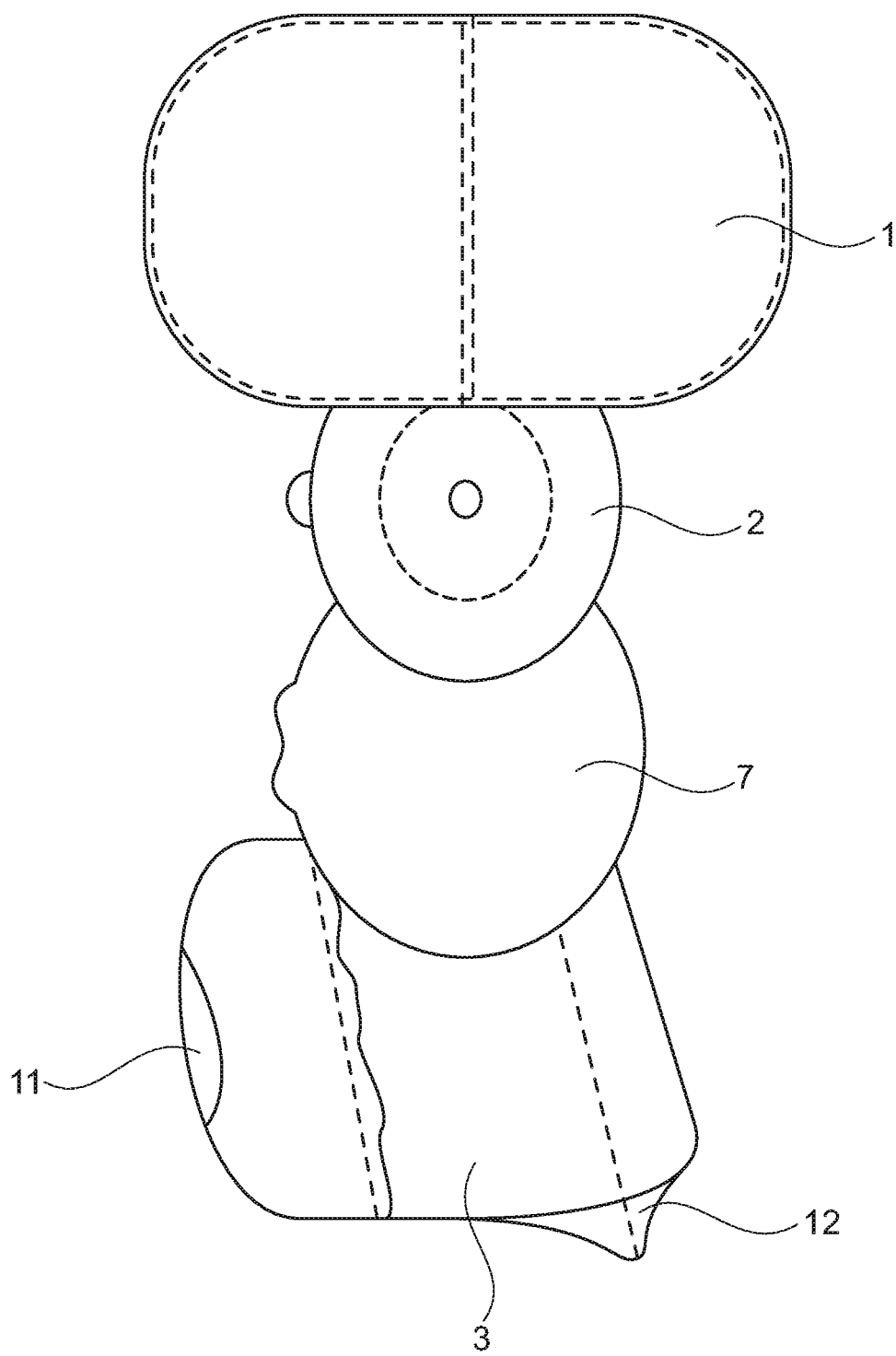
In FIG. 4 is shown an ostomy appliance with a self-standing release liner.
Figure 5:
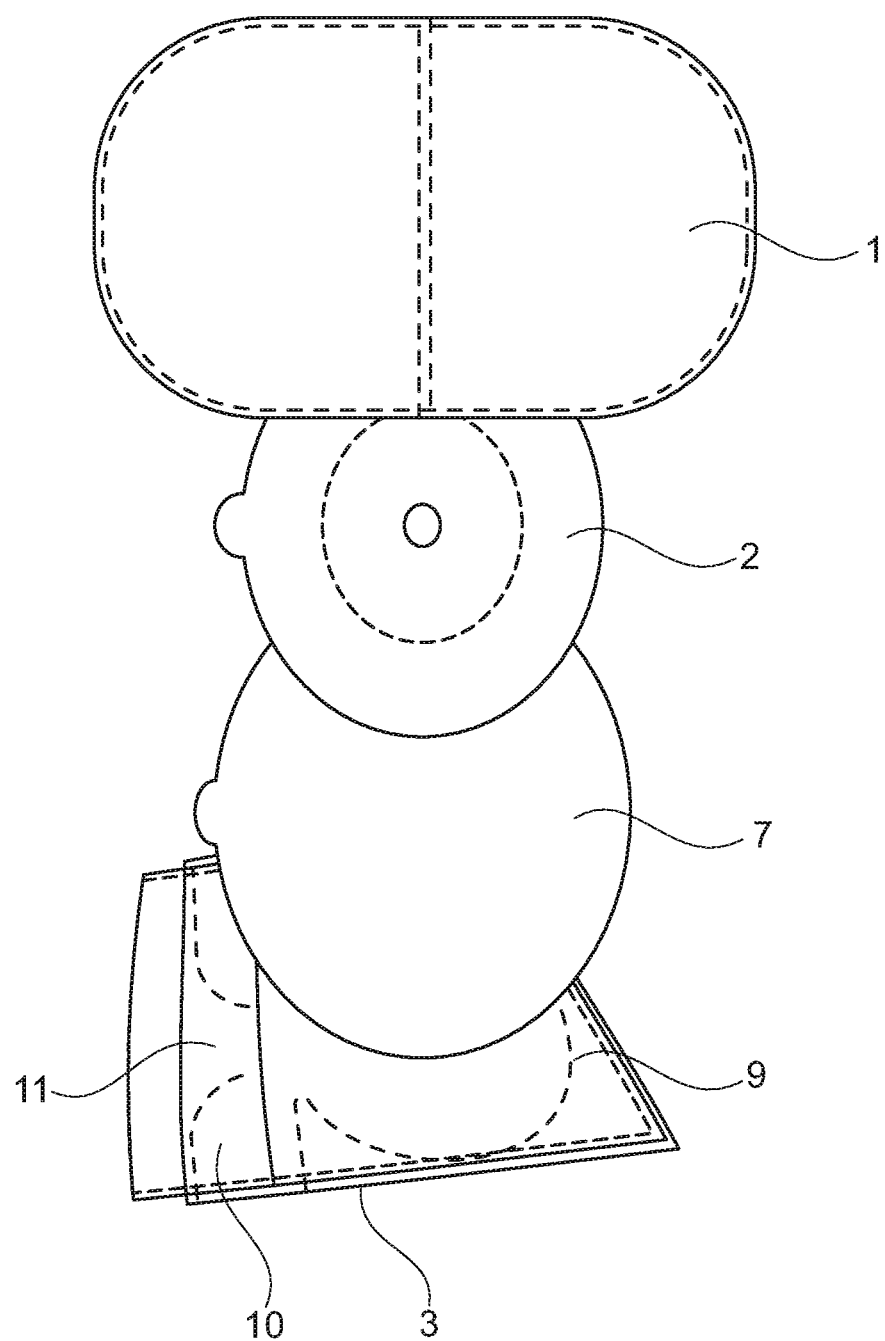
In FIG. 5 is shown an ostomy appliance with a release liner suitable for use in horizontal position.

In FIG. 4 is shown an exploded view of an appliance with a self-standing release liner 3 where the enclosure is provided with a foot 12 enabling stability at vertical position. In FIG. 5 is shown an appliance with a release liner 3 suitable for use in horizontal position.

Figure 6A:
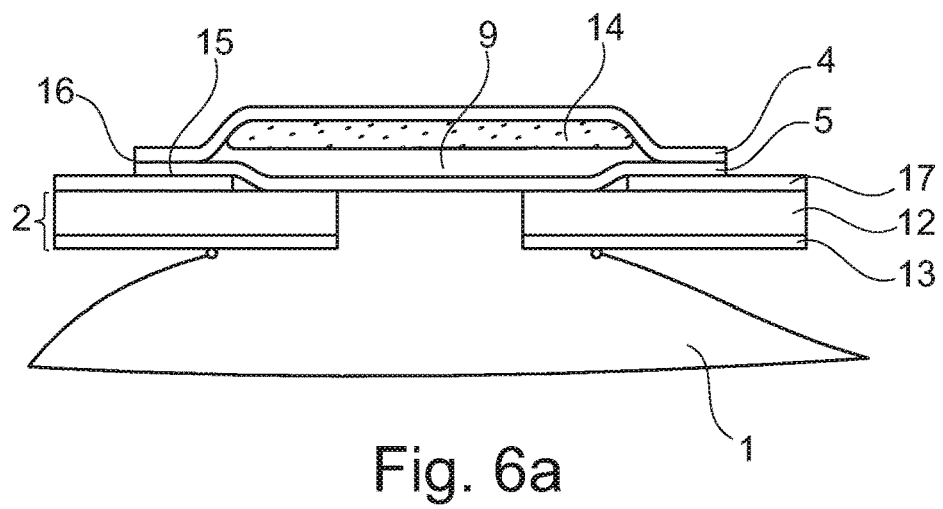
FIGS. 6a to 6c show an embodiment of an ostomy appliance with a release liner capable of containing a wipe.
Figure 6B:
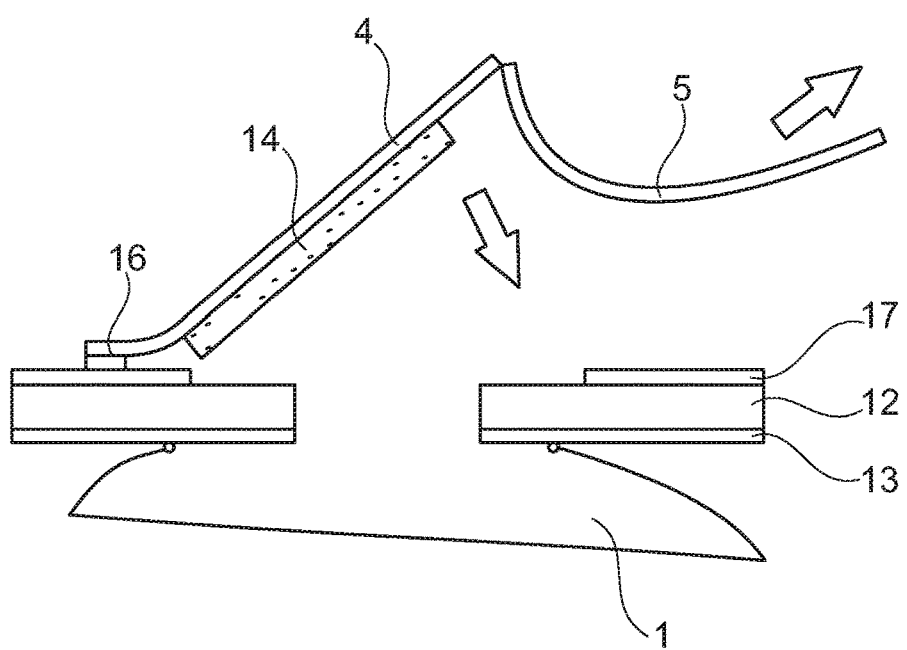
Figure 6C:
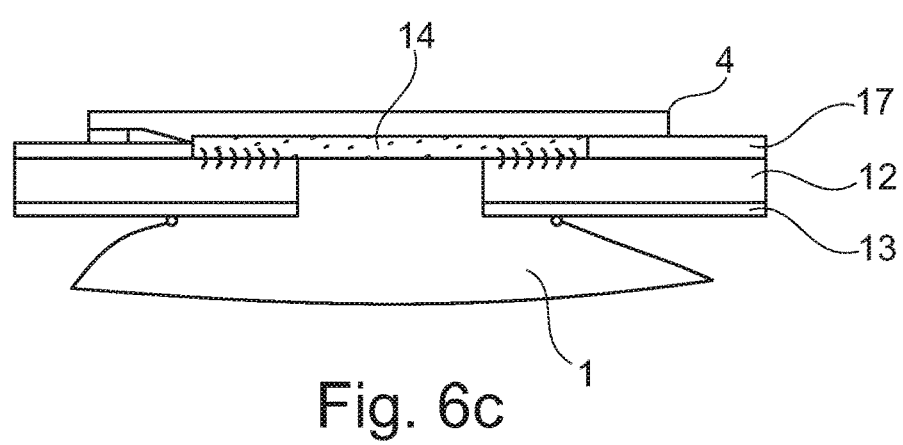

In FIGS. 6a to 6c are shown a cross section of an ostomy appliance comprising an adhesive wafer in the form of a backing layer 13 coated with an adhesive layer 12. On the distal surface of the backing layer 13 is provided a collection bag 1. The bag 1 may be detachable or permanently fixed to the wafer. The adhesive layer 12 may be in the form of one or more different adhesives, such as a first adhesive at the central portion of the wafer and a second adhesive at the peripheral portion of the wafer.

The peripheral section of the proximal adhesive surface of the wafer is covered with a first release liner 17. The central portion of the adhesive surface of the wafer is covered with a second release liner 3 comprising an enclosure 9. The second release liner 3 at least partly overlaps the first release liner 17 along the inner edge portion of the first release liner.

The second release liner 3 is defined by a first 4 and a second wall 5 being sealed together along the edge to form an enclosure 9, and the enclosure containing a wipe 14. The wipe 14 may be attached to the first wall 4. The wipe 14 is impregnated with an activating agent.

Before use of the appliance, the second release liner (with the enclosure) 3 is released from the adhesive at the periphery (the release point may be provided with a tab member for easy gripping—not shown on the FIG.) and lifted away from the adhesive and pivoted over a hinge point 16 at the opposite periphery. The second sheet 5, being the sheet closest to the wafer is then removed and the first sheet 4, to which the wipe 14 is attached, is lowered again towards the adhesive surface and the wipe 14 is brought in contact with the adhesive. The activating agent of the wipe 14 may activate the adhesive being in contact with the wipe 14 and the second release liner 3, including the wipe 14 can then be removed and the wafer attached to the skin.

Figure 7A:
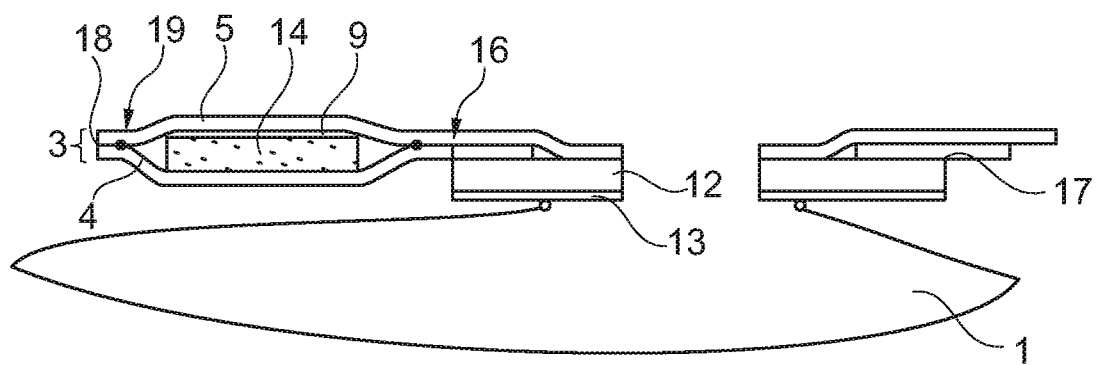
FIGS. 7a to 7d show an embodiment of an ostomy appliance with a release liner capable of containing a wipe.
Figure 7B:
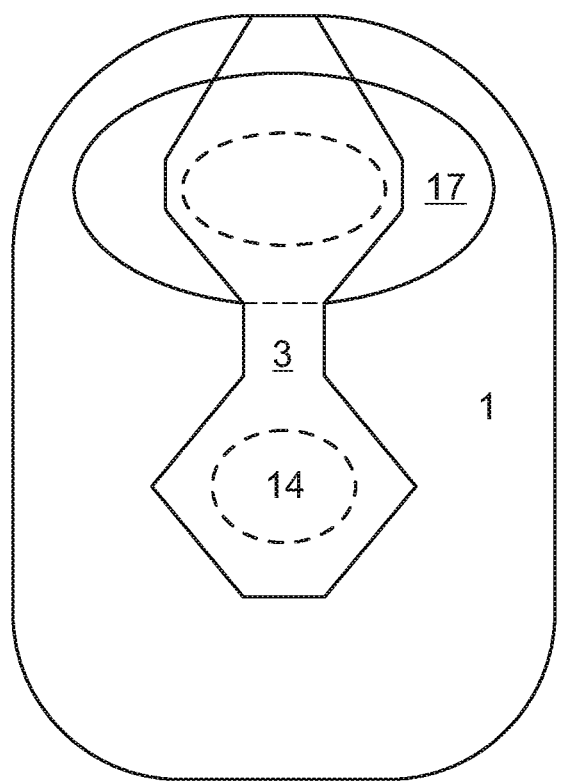

FIGS. 7a to 7d illustrate a further embodiment of an ostomy appliance. FIG. 7a illustrates a cross-sectional view of the appliance prior to use. Like in the embodiment of FIG. 6a to 6c, the appliance is provided with a wafer comprising a backing layer 13 with adhesive 12. The bag 1 is permanently or detachably attached to the backing layer. The adhesive 12 is provided with a first annular release liner 17 covering the outer part of the adhesive. Furthermore, a second release liner 3 including an enclosure 9 is attached to the appliance. The second release liner 3 has a first wall 4 attached to the first release liner 17 at a lower edge of the first release liner—that is towards the bottom of the bag in the normal use of the bag. The attachment may be rupturable attachment and provides a hinge point 16 that will be explained further in the following. Folded on top of the first wall and covering the first wall as well as the central part of the adhesive and part of the first release liner is a second wall 5. The first wall 4 and the second wall 5 are connected at a rupturable connection 18 and sealed together at an annular seal 19 so they provide an enclosure 9. The seal 19 may be an adhesive or welded seal; however, it should be peelable. The enclosure 9 includes a wipe 14 with an activating agent. FIG. 7b illustrates the appliance prior to use but seen from the rear wall. In FIG. 7b it can be seen that the second wall 5 covers only the middle part of the first release liner.

Figure 7C:
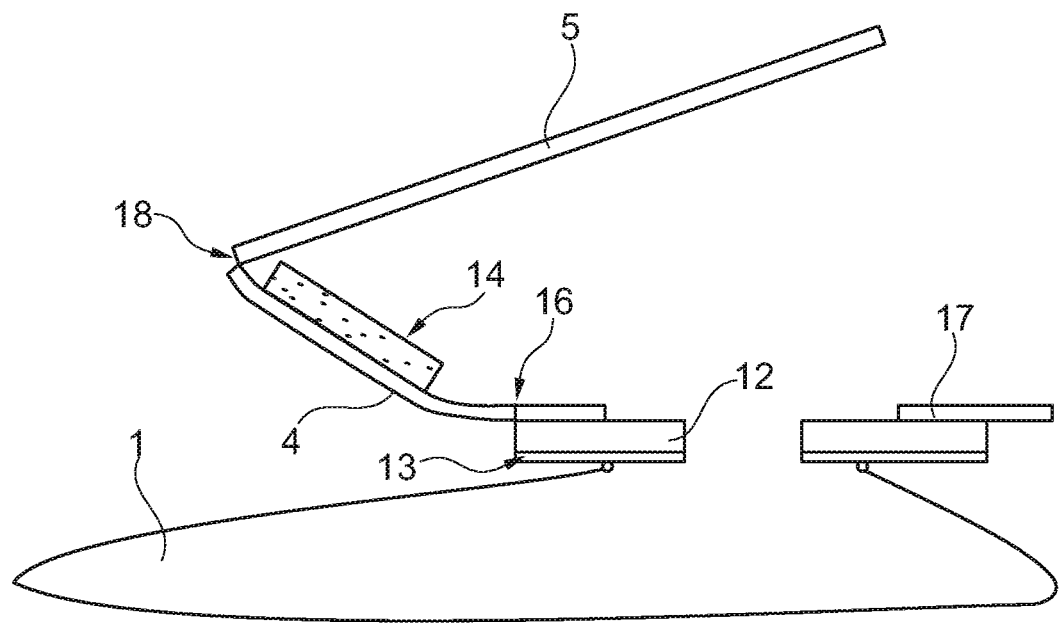

FIG. 7c illustrates the appliance as the use is being prepared. The second wall 5 has been lifted up from the first wall 4 and the central part of the adhesive has been uncovered. The second release liner is beginning to pivot around the hinge point 16 by gripping at the second wall. Alternatively, the second wall may be separated from the first wall by rupturing the rupturable connection 18 and the user may then grip at the end of the first wall thereby pivoting the second release liner around the hinge point 16.

Figure 7D:
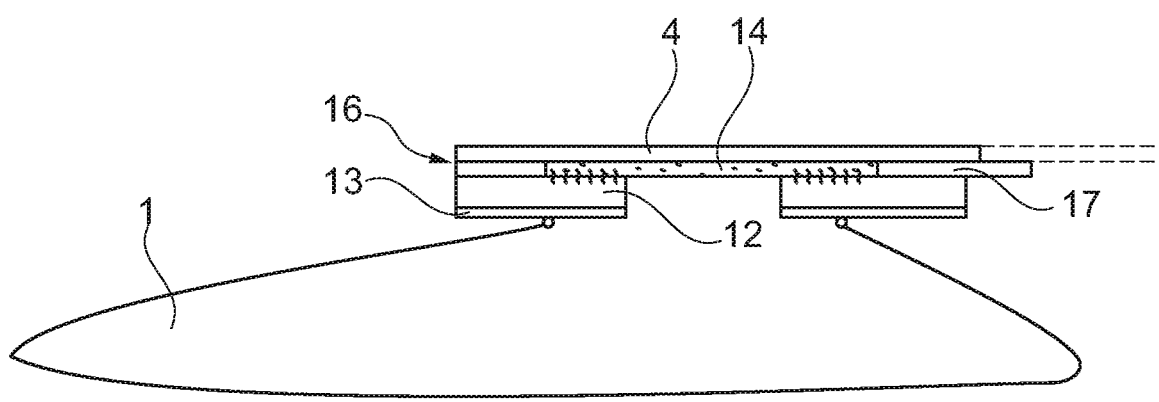

FIG. 7d illustrates the position, where the wipe 14 has been brought into contact with the central part of the adhesive. In this position the first wall 4 of the second release liner overlays the first release liner 17.

To make the final preparation for use, the first and second release liner as well as the wipe are removed from the adhesive 12 of the appliance. Thereby the adhesive is prepared and can be brought into contact with the abdominal surface of the user.

EXAMPLES

In embodiments, the dimensions of the enclosure of the release liner may depend on the size (adhesive surface area) of the adhesive wafer. In the following examples, the release liner was designed to fit an adhesive wafer being oval and having the dimensions of 120×100 mm.

Example 1

Preparation of a Self-Standing Release Liner

A release liner was prepared having outer dimensions of 150×200 mm. A clear PE (polyethylene) film with a thickness of 0.1 mm was chosen for the release liner in order to provide stability and good weldability. Welding of the enclosure as well as other welding lines were conducted at 180 degrees for 1.5 seconds and a pressure of 2 bar.

The enclosure was provided with a foot for enabling self-standing. The foot was prepared by folding the lower part of the enclosure 20 mm up and in to itself and then welding the sides with the above specified welding parameter.

The film for the release liner was siliconized on the outer side (surface outside the enclosure). The inner side (surface inside the enclosure) was not siliconized in order not to inhibit welding. Siliconization was a type 1803 from Hutamaki with a tight release in order to provide a good adherence to the adhesive before use and an easy removal after heating when application of the wafer to the skin was initiated.

At the top of the enclosure, a funnel shaped inlet was provided, enabling easy filling of the enclosure with liquid. The inlet may also comprise a non-return valve prepared as described more in detail in Example 2. A non-return valve may provide a substantially fluid tight seal of the enclosure for extra security, in order to avoid spillage in case the self-standing wafer and release liner was accidentally tilted and brought to a non-vertical position.

Example 2

Preparation of a release liner suitable for use in horizontal position.

A release liner was prepared as in Example 1 except the enclosure was not provided with a foot. A non-return valve was made at the top of the enclosure by inserting a centre film in the top of the enclosure, the centre film had the same width as the enclosure (150 mm) and a height of 50 mm. This film was welded with the side edges of the enclosure and a funnel shaped welding of all three films from the top of the enclosure. The depth of the welding was only 40 mm deep in to the enclosure so that 10 mm of the centre film was not welded. As this welding was stopped when a 20 mm void in the centre was obtained, liquid can enter into the enclosure through this, but cannot enter out of the enclosure, as the 10 mm non welded film will seal the void when liquid try to pass back. Liquid may push the two films together and seal the void. When the enclosure was brought into a non-vertical position such as placing the enclosure horizontally on the table or other surface the liquid did not leak from the enclosure.

When water is poured in to the enclosure, air may be trapped inside the enclosure, not being able to pass the non-return valve. If the amount of trapped air in the enclosure is too large, there is a risk that the adhesive will not be fully exposed to the warm water as intended. In this example, an air compartment was provided in fluid connection with the enclosure. This air compartment was made by a welding from both sides of the enclosure at approximately 40 mm lower than the end of the non-return valve so that approximately 40 mm non welded void in the center is obtained. Liquid and air can freely flow in and out of the void. When the enclosure was placed on a horizontal surface, the trapped air will move to the air compartment and the liquid will be in both compartments. No air was present in the compartment covering the adhesive, thus the entire adhesive surface was exposed to the temperature impact from the liquid.

When placing the wafer in lying (horizontal) position, the wafer is first held upright with the lower part of the appliance resting on the surface to be laid on (such as a table). Then the rest of the appliance is brought in contact with the table by slowly lowering the wafer. In this way, the enclosure will be filled with liquid and the air will be pushed into the air compartment, optionally together with some of the liquid.

In this example, a volume restricting feature (anti-ballooning means) is provided by welding a 10 mm dot in the middle of the enclosure centrally placed for the adhesive surface of the wafer. This prevents the enclosure for expanding in to a balloon shape. This feature saves liquid and makes the product less bulky.

The invention claimed is:

1. An ostomy appliance comprising:
   an adhesive wafer for securing the ostomy appliance to skin of a user, the adhesive wafer comprising an adhesive layer, a backing layer applied to a distal surface of the adhesive layer, and a release liner applied to a proximal surface of the adhesive layer;
   wherein said release liner comprises an enclosure adapted to contain a liquid.

2. The ostomy appliance according to claim 1, wherein the release liner comprises one or more layers of polymer film sealed together to form the enclosure.

3. The ostomy appliance according to claim 1, wherein the enclosure includes a first wall sealed to a second wall along a periphery of the first wall and the second wall, and a weld line is provided coupling the first wall to the second wall with an opening provided by the weld line that forms an inlet into the enclosure.

4. The ostomy appliance according to claim 3, wherein the inlet comprises sealing means for sealing of the enclosure.

5. The ostomy appliance according to claim 3, wherein the inlet includes a one-way valve allowing flow into the enclosure and preventing flow out of the enclosure.

6. The ostomy appliance according to claim 5, wherein the one-way valve is formed by a fold line applied one of the first wall and the second wall.

7. The ostomy appliance according to claim 1, wherein enclosure includes a first wall sealed to a second wall along a periphery of the first wall and the second wall, and a weld line is provided coupling the first wall to the second wall to form a funnel inlet into the enclosure.

8. The ostomy appliance according to claim 1, wherein an exterior wall of the release liner includes a foot that is adapted to allow the ostomy appliance to be self-standing when the enclosure is filled with the liquid.

9. The ostomy appliance according to claim 1, wherein the adhesive is a temperature-sensitive adhesive that is adapted to be sensitive to temperature changes.

10. The ostomy appliance according to claim 1, wherein the release liner comprises an air compartment in fluid connection with the enclosure.

11. The ostomy appliance according to claim 1, further comprising a wipe sheet of absorbing material retained in the enclosure.

12. The ostomy appliance according to claim 1, wherein the adhesive layer includes a stoma-receiving hole formed through a thickness of the adhesive layer and a region of adhesive surrounding the stoma-receiving hole, and the enclosure is provided with a sheet of absorbent material and includes a removable wall separating the sheet of absorbent material from the region of adhesive surrounding the stoma-receiving hole.

\* \* \* \* \*

UNITED STATES PATENT AND TRADEMARK OFFICE
CERTIFICATE OF CORRECTION

PATENT NO. : 11,109,996 B2
APPLICATION NO. : 15/761812
DATED : September 7, 2021
INVENTOR(S) : Stroebech et al.

Page 1 of 1

It is certified that error appears in the above-identified patent and that said Letters Patent is hereby corrected as shown below:

In the Specification

In Column 3, Line 66, delete "liner and" and insert -- liner, and --, therefor.

In Column 4, Line 39, delete "use." and insert -- to use. --, therefor.

In Column 5, Line 18, delete "liner and" and insert -- liner, and --, therefor.

In Column 7, Line 15, delete "in to" and insert -- into --, therefor.

In Column 7, Line 47, delete "in to" and insert -- into --, therefor.

In Column 7, Line 57, delete "in to" and insert -- into --, therefor.

In Column 8, Line 19, delete "in to" and insert -- into --, therefor.

In the Claims

In Column 8, Line 45, in Claim 6, delete "applied" and insert -- applied to --, therefor.

In Column 8, Line 47, in Claim 7, delete "wherein" and insert -- wherein the --, therefor.

Signed and Sealed this
Seventh Day of December, 2021

Drew Hirshfeld
*Performing the Functions and Duties of the
Under Secretary of Commerce for Intellectual Property and
Director of the United States Patent and Trademark Office*